(12) United States Patent
Behari

(10) Patent No.: US 10,725,010 B2
(45) Date of Patent: Jul. 28, 2020

(54) INTEGRATED AND MODULAR ROBOTIC PLATFORM FOR TESTING AND MONITORING SURFACE WATER QUALITY

(71) Applicant: Meghna Behari, Sewickley, PA (US)

(72) Inventor: Meghna Behari, Sewickley, PA (US)

( * ) Notice: Subject to any disclaimer, the term of this patent is extended or adjusted under 35 U.S.C. 154(b) by 160 days.

(21) Appl. No.: 16/122,085

(22) Filed: Sep. 5, 2018

(65) Prior Publication Data

US 2019/0072533 A1 Mar. 7, 2019

Related U.S. Application Data

(60) Provisional application No. 62/554,073, filed on Sep. 5, 2017.

(51) Int. Cl.
*G01N 33/18* (2006.01)
*H04W 4/02* (2018.01)
(Continued)

(52) U.S. Cl.
CPC ............. *G01N 33/18* (2013.01); *B63B 35/00* (2013.01); *B63C 11/52* (2013.01); *G08C 17/02* (2013.01);
(Continued)

(58) Field of Classification Search
CPC .... G01C 13/00; G01C 13/008; G01C 13/002; G01C 13/004; G01C 13/006; G01C 5/06; G01N 33/1886; G01N 33/18; G01N 2001/021; G01N 1/10; G01N 1/16; G01N 33/1806; G01N 1/14; G01N 2021/6432; G01N 2021/6434; G01N 21/78; G01N 21/80; G01N 33/1826; G01N 33/24; G01N 3/42; G01N 15/04; G01N 17/008;
(Continued)

(56) References Cited

U.S. PATENT DOCUMENTS 4,157,657 A * 6/1979 Hinchman ......... G01N 33/1886
254/333
6,119,630 A * 9/2000 Lobsiger ............ G01N 33/1886
119/238
(Continued)

FOREIGN PATENT DOCUMENTS

CN 201109479 Y 9/2008
CN 101806811 A 12/2012
(Continued)

*Primary Examiner* — Andre J Allen
(74) *Attorney, Agent, or Firm* — David G. Oberdick

(57) ABSTRACT

An aquatic robotic assembly for testing and monitoring water quality parameters including a waterproof base with a remote-controlled motor assembly, a propulsion assembly, a power source, and a flotation assembly. The aquatic robotic assembly also includes at least one waterproof upper module that detachably connects to the base and includes a sensor assembly, the sensor assembly comprising at least one sensor for use in testing and monitoring a water quality parameter, a micro-computer interconnected with the at least one sensor for reading input from the at least one sensor and converting the data to a format readable by a user, a wireless transmitter for transmitting the converted data to the user, and a power source. Alternative upper modules can be used with different sensor assemblies.

12 Claims, 11 Drawing Sheets

(51) Int. Cl.
  *B63B 35/00* (2020.01)
  *B63C 11/52* (2006.01)
  *G08C 17/02* (2006.01)
  *B25J 19/02* (2006.01)
  *B25J 13/00* (2006.01)

(52) U.S. Cl.
  CPC ............... *H04W 4/02* (2013.01); *B25J 13/006* (2013.01); *B25J 19/02* (2013.01)

(58) Field of Classification Search
  CPC .......... G01N 1/04; G01N 1/18; G01N 1/2035; G01N 1/22; G01N 2015/0088; G01N 2021/1772; G01N 2021/1793; G01N 2021/4769; G01N 2021/556; G01N 2033/1873; G01N 2035/00881; G01N 21/15; G01N 21/55; G01N 2203/0082; G01N 2203/0682; G01N 33/246; G01N 3/064; G01N 3/34; G01N 7/14; G01N 1/12; G01N 21/763; G01F 1/002; G01F 1/005; G01F 23/00; G01F 23/292; G01F 23/303; G01F 23/56; G01F 23/58
  USPC .......................................... 73/170.29–170.34
  See application file for complete search history.

(56) References Cited

U.S. PATENT DOCUMENTS

| | | | | |
|---|---|---|---|---|
| 6,523,426 | B1* | 2/2003 | Vincent | G01N 33/18 204/408 |
| 2005/0118704 | A1* | 6/2005 | Malobabic | G01N 35/00871 435/287.1 |
| 2013/0285821 | A1* | 10/2013 | Nakamura | G01N 27/622 340/603 |
| 2014/0299526 | A1* | 10/2014 | Mastio | C02F 1/008 210/94 |
| 2016/0272291 | A1* | 9/2016 | Outa | B63G 8/14 |
| 2017/0234848 | A1* | 8/2017 | Cheng | G01N 21/17 73/61.41 |
| 2018/0059085 | A1* | 3/2018 | Anderson | G01N 33/1886 |
| 2018/0088099 | A1* | 3/2018 | Starr | F16L 55/34 |
| 2019/0285606 | A1* | 9/2019 | Starr | F16L 55/34 |

FOREIGN PATENT DOCUMENTS

| | | | |
|---|---|---|---|
| CN | 102999047 B | 3/2013 | |
| CN | 102227119 A | 1/2014 | |
| CN | 204405643 U | 6/2015 | |
| CN | 103213662 A | 7/2015 | |
| KR | 1618625 B1* | 5/2016 | ............ G01N 1/286 |

* cited by examiner

INTEGRATED AND MODULAR ROBOTIC PLATFORM FOR TESTING AND MONITORING SURFACE WATER QUALITY

CROSS-REFERENCE TO RELATED APPLICATIONS

This application claims priority to U.S. Provisional Application Ser. No. 62/554,073, filed Sep. 5, 2017, which application is incorporated by reference herein in its entirety.

STATEMENT REGARDING FEDERALLY SPONSORED RESEARCH

Not applicable.

FIELD OF INVENTION

The present invention is an integrated and modular robotic platform for testing and monitoring surface water quality.

BACKGROUND

Globally, the lack of clean water poses a significant problem; however, this problem can begin to be solved by frequent analysis of the quality of water. The present invention is a novel solution to all current water quality testing needs and an improvement over current testing devices and methods. Traditional methods include hand-held meters, data logging machines, or the process of collecting samples and testing them in a lab. The limitations of these traditional methods are discussed below.

Hand-Held Sensors: Hand held sensors are portable sensory devices that only can test for a limited number of chemicals per device. They must be calibrated before each use. They can be fairly inexpensive (depending on the chemical being tested by the sensor). The price for such sensors can range from $20.00 to well over $1,000.00. These sensors are good for simple at-home tests and, for more expensive sensors, can be used for more advanced testing in a laboratory or clinical testing. Stated differently, a user can pick a sensor that best suits the user's needs, but such sensors can become expensive. Moreover, these sensors are extremely inconvenient to use it for testing in field settings, and they are not able to access hard-to reach parts of waterways.

Data Logging Machine: Data logging machines are complex box-like machines that sit in the banks of rivers, creeks, lakes, etc. For a long period of time, they remain in the water and gather huge amounts of data. The data logging machines can test for several chemicals and do not have a time limit on how long they can sit in the water. These machines are very expensive, as prices normally run in the thousands of dollars (depending on the quality of the machine). Such machines are appropriate for water-quality inspectors looking to gather data for a particular case or inquiry, or for scientists using the data for scientific research. It is not an appropriate device for household tests and is out of the price range for most people.

Collection and Analysis of Samples: Collecting samples from each waterway and taking the samples back to a lab for analysis (whether by the user or a third party scientist or technician) can be a long and inconvenient process. For water-quality inspectors who have to do this process on a weekly-basis, it is inconvenient and can take up to a week long. While this process is relatively inexpensive (depending on access to a lab or lab resources), it can be even more time-consuming for at-home users to go through such a long process.

The Aquabot of the present invention is positive improvement and solution to these three traditional methods because the Aquabot incorporates the positive aspects of each, and Aquabot can be utilized by a wide variety of users. Aquabot can provide accurate data on several water quality parameters in a convenient and efficient way. Further, Aquabot can be used by both scientists and citizens.

BRIEF SUMMARY OF THE INVENTION

The present invention, in a preferred embodiment, is a robotic, modular device adapted to simplify water quality testing. The device of the present invention is organized in a modular system, is preferably remote-controlled robot, and is capable of collecting data on several surface water parameters. The collected data on water quality parameters can be sent wirelessly to a computer or smartphone app. The user can also receive data through other methods such as as an LCD and LED interface to allow for quick assessment of water quality. In one embodiment, coordinates of the testing locations are recorded via a GPS module and sent to either a computer or smartphone.

BRIEF DESCRIPTION OF THE DRAWINGS

Embodiments of the present invention will now be described, by way of example only, with reference to the accompanying drawings for the purpose of illustrating the embodiments, and not for purposes of limiting the invention, wherein.

DETAILED DESCRIPTION OF THE INVENTION

Figure 1:
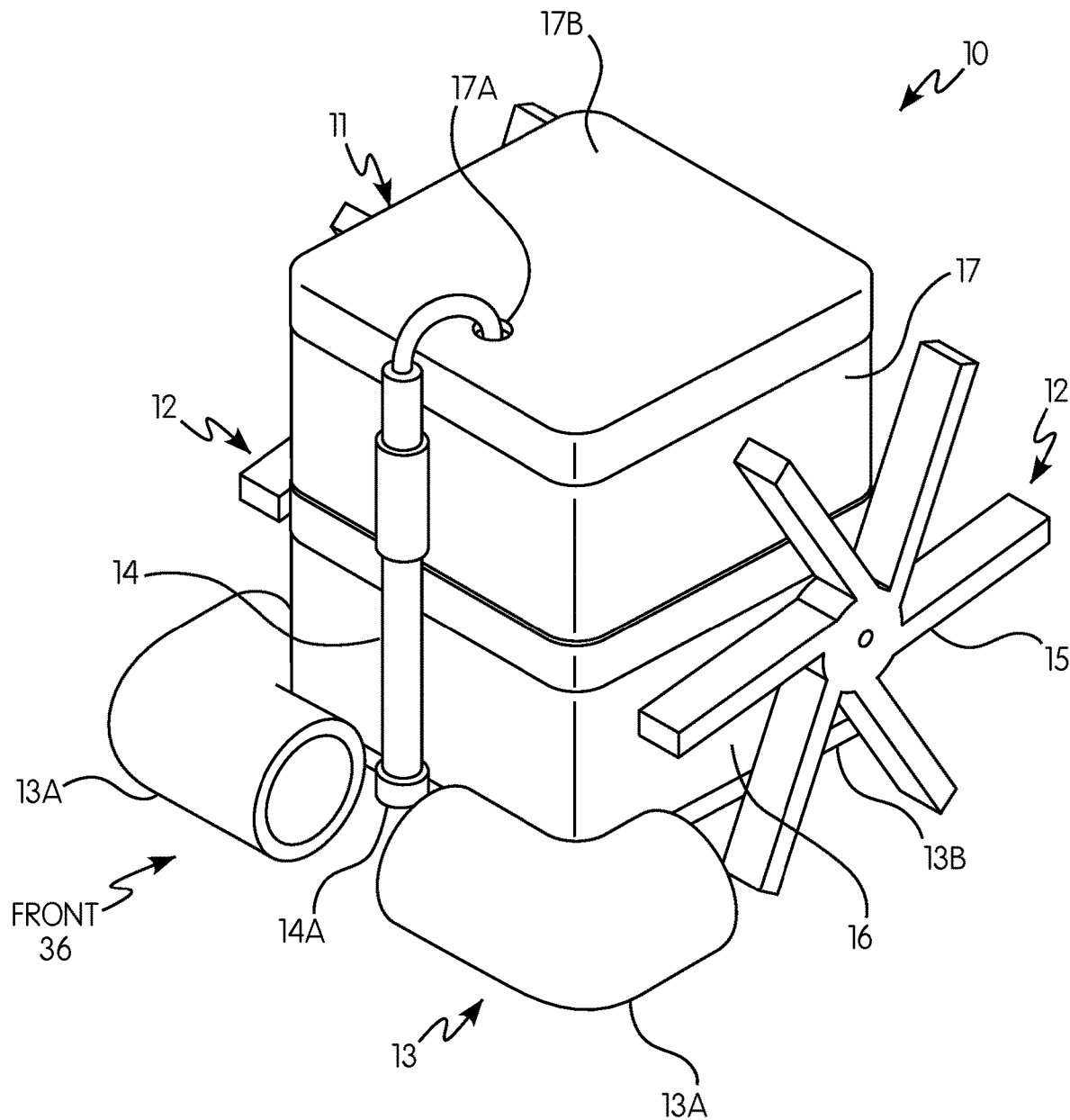
FIG. 1 is a top front perspective view of one embodiment of the aquatic robot device of the present invention.
Figure 2:
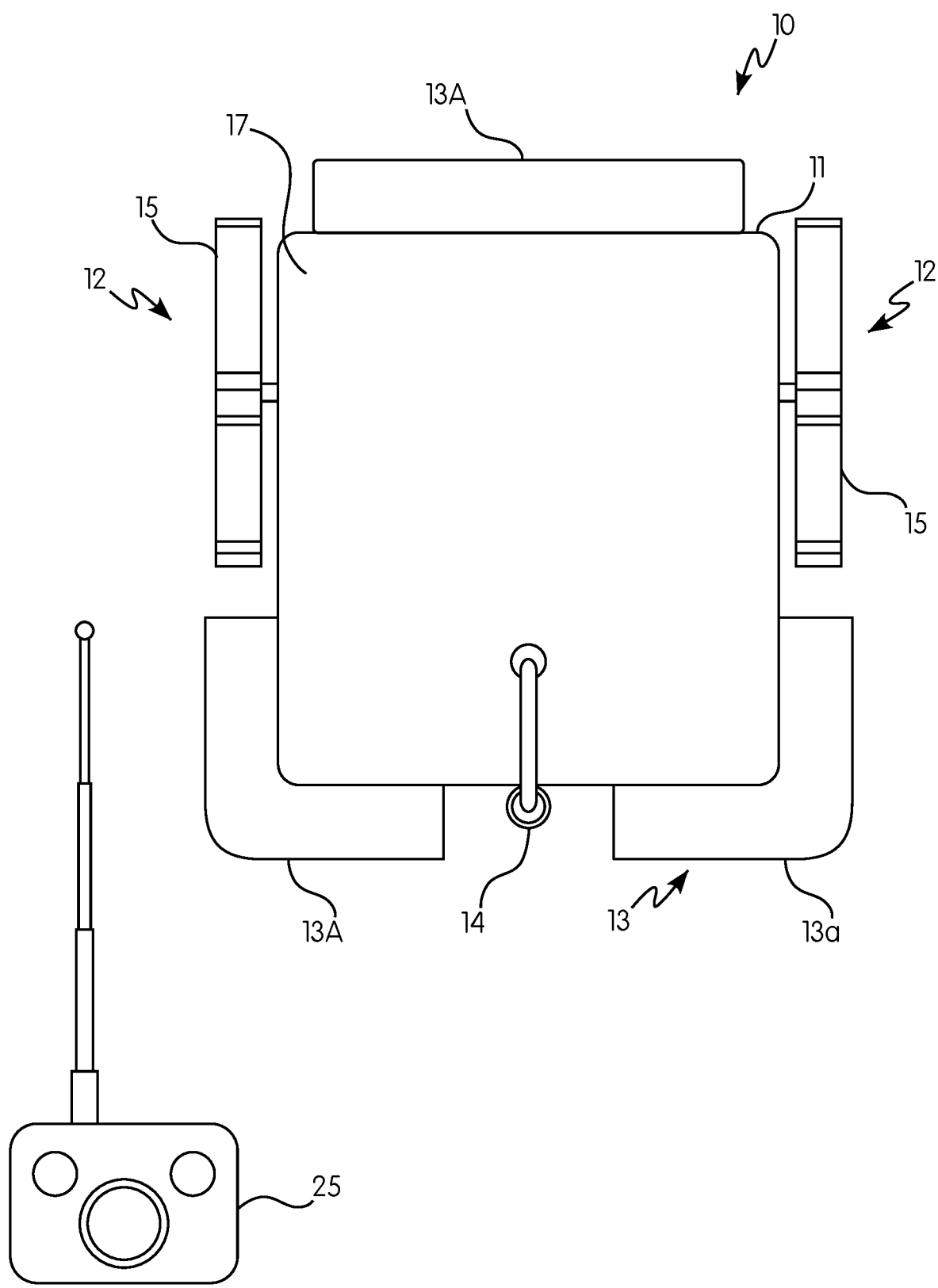
FIG. 2 is a top view of the device shown in FIG. 1, along with a remote controller.

As generally shown in FIGS. 1-11, the aquatic robot or "Aquabot" of the present invention is a robotic device 10 with an online platform that simplifies water quality testing and logging/recording. As shown in FIGS. 1 and 2, device 10, in one embodiment, includes a water-proof housing or body 11 with an upper module 17 and a lower module or base 16, a propulsion assembly 12, a flotation assembly 13 and one or more testing sensors 14 associated with upper module 17. Upper module 17 is removable so that alternative modules 17, with other sensors 14, can be interchangeably used with device 10.

Figure 4:
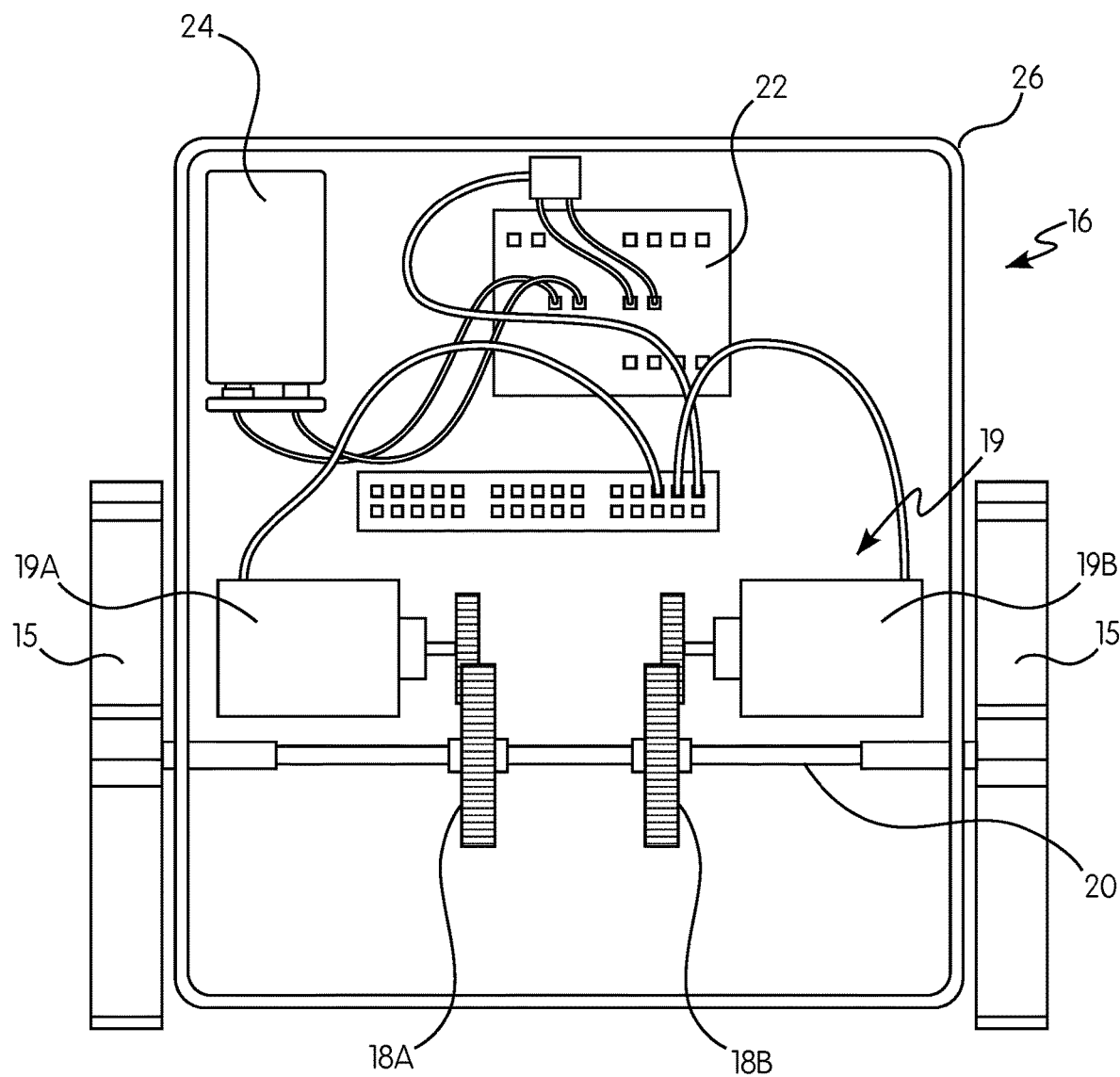
FIG. 4 is a top view of the lower module or base of the device shown in FIG. 1.
Figure 5A:
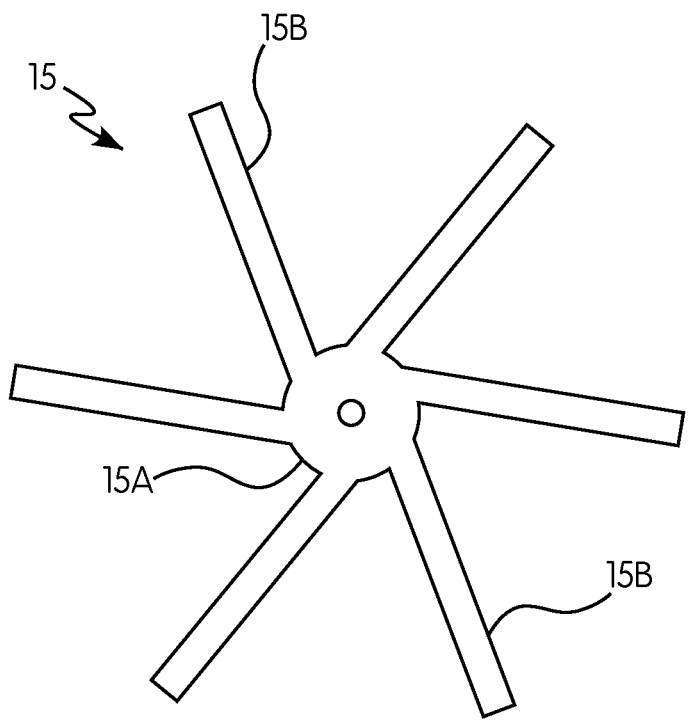
FIG. 5A is a side view of one embodiment of the propeller for the device shown in FIG. 1.
Figure 5B:
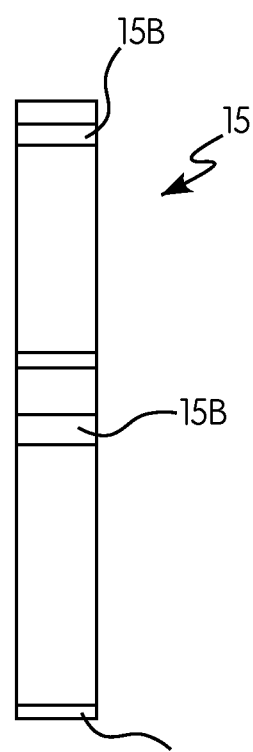
FIG. 5B is a top view of one embodiment of the propeller for the device shown in FIG. 1.
Figure 5C:
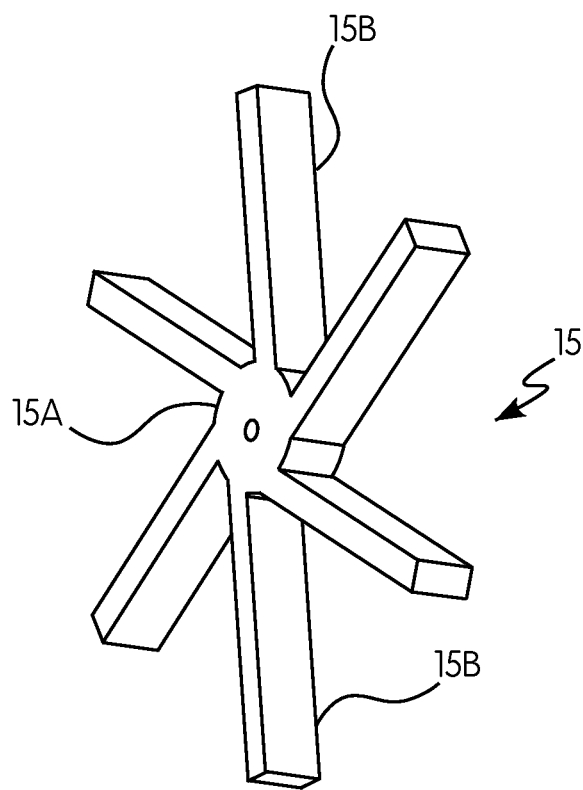
FIG. 5C is a perspective view of one embodiment of the propeller for the device shown in FIG. 1.

In the embodiment shown in FIG. 4, lower module or base 16 of device includes a motor system 19 for powering and moving device 10 in water. In this embodiment, the motor system 19 is comprised of dual, brushless, hobby motors 19A and 19B for powering an axle 20 with propellers 15 on opposite ends of lower module or base 16. In the embodiment shown in FIGS. 5A-5C, the propulsion assembly 12 can include propellers 15, each with a circular center 15A with blades or slats 15B extruded from the center 15A at an angle, which provides a design fit to reduce water resistance. Other propeller designs or methods of locomotion in water can be used without deviating from the purpose and function of the device. In this same embodiment shown in FIG. 4, a remote control chip 22 is wired to the motor system 19, which allows for wireless operation through remote controller 25 (FIG. 2). The motor system 19 is placed in a waterproof module or container 26, which acts as the outer body for the lower module. Container 26 can be comprised of plastic or other light-weight waterproof material. The lower module or base 16 also includes a power supply, such as a battery 24. Other known power supplies also can be used, such as a solar cell. In addition, a flotation assembly 13, with multiple floats 13A and 13B, are attached to the lower module 16 in one embodiment.

Figure 3:
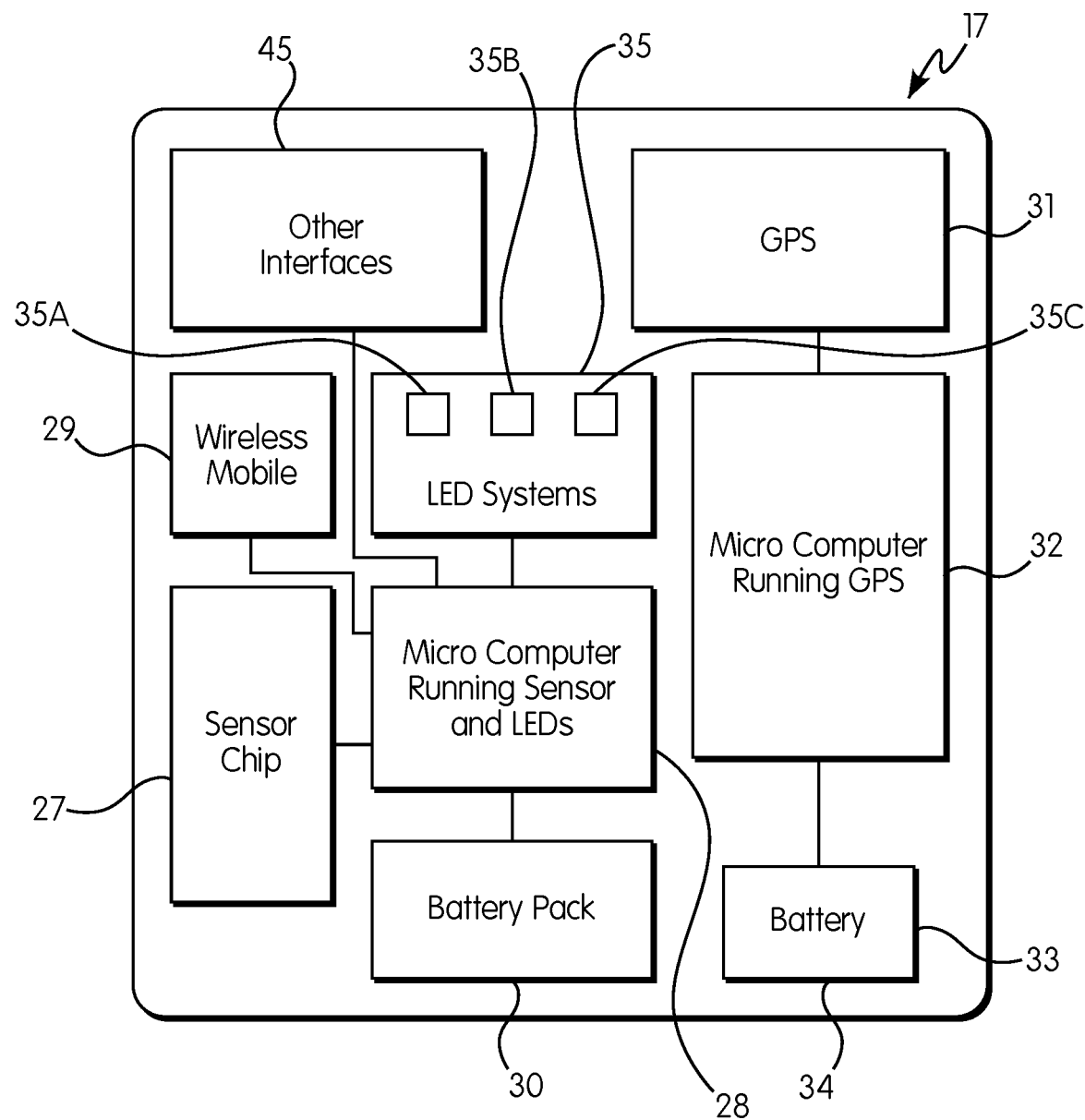
FIG. 3 is a block diagram of the upper module of the device shown in FIG. 1.

In the embodiment shown in FIG. 3, upper module 17 is comprised of various components holding the software for use with data interfaces and sensors 14 associated with the device 10. The device 10 collects data from one or more sensors 14 located on the exterior of device 10 and exposed to the water. In one embodiment, the sensors 14 are sensitive electrodes, but other sensors known to those with skill in the art can be used. Each sensor 10 connects to a sensor chip 27, which, in turn, connects to an Arduino (a micro-computer) 28 that converts the sensor readings into respective water testing parameter. For example, voltage readings from the sensors 14 can be converted into applicable parameters. In a preferred embodiment, the device 10 can test for pH, oxidation reduction potential, total dissolved solids, conductivity, salinity, ammonia, nitrite, nitrate, and specific gravity. Each sensor 14 can be placed in a different detachable and interchangeable module 17, allowing the user to switch out the sensors 14 being used and the water parameters being tested, and thereby adapt to the testing needs of the user. However, more than one sensor 14 may be incorporated into a single detachable module 17. Similar to lower module or base 16, upper module 17 is placed in a waterproof module or container 33, which acts as the outer body for the lower module or base. Container 33 can be comprised of plastic or other light-weight waterproof material and can have any shape or size.

In one embodiment, each of the one or more sensors 14 of the device 10, when in use, is interconnected, through micro-computer 28, to a wireless module 29, which allows the collected data, after conversion, to be wirelessly conveyed and displayed on a serial monitor. Wireless transmission can be made using Bluetooth® or other similar technologies. Sensor chip 27, micro-computer 28, and wireless module 29 are powered by battery pack 30. Other known power supplies also can be used, such as a solar cell. Through this wireless interface, device 10 can be compatible with a smartphone or other smart device application, which receives sensor data that is collected by device 10 through wireless module 29, whereby the sensor data appears on the associated smart device screen in real time. Using a compatible application, a user also can manually enter a parameter that was tested, and all the associated data can be saved under that parameter, along with the associated date and location of collection. The data thereafter can be accessed at any time by the user.

A GPS module 31 is also incorporated in one embodiment, such that the device 10 displays the time, date, location, and altitude of where the data is collected. GPS module 31 is interconnected with an Arduino or micro-computer 32 and a power supply such as battery 33. GPS module 31 also can attach to and be powered by battery pack 30 (which can power all components. GPS module 31 can have its own wireless component using, for example but without limitation, currently existing pre-made GPS chips that have a built-in wireless device that can connect to a computer. Alternatively, GPS module 39 can interconnect with wireless module 29.

In a further embodiment, upper module 17 of device 10 also includes an LED interface 35, which is interconnected with micro-computer 28 and can consist of three LED lights (red 35A, green 35B, and yellow 35C) located in the upper module 17 of device 10. The lights blink in a predetermined pattern to provide a visual signal of water test results. For example, the LED lights can blink red if a certain parameter is too high; yellow, if the parameter is too low; or green, if the parameter is ideal or healthy. Other interfaces can be incorporated into upper module 17, as discussed more fully below. LED interface 35 and other interfaces are powered by battery pack 30.

Each of the components and features of the aquatic robot device 10 are discussed in further detail below.

Modular Components. As discussed above, the aquatic robot device 10 preferably has two modules, i.e., a lower module or base 16 and an upper module 17. In other embodiments, the device can include further upper modules. In one embodiment, each of the modules 16 and 17 has a water-tight outer container 34 and 26, respectively, which can be, for example, a plastic box-like container. Both containers can have varying shapes and sizes. The lower module or base 16—the module closest to the water—contains the motor system 19. The propellers 15 extend from the lower module or base 16 and contact the water in which the device 10 is placed (the flotation assembly 13 is also in contact with the water). The upper module 17 or modules contain the micro-computers 28 and 32 that contain the programming for running and reading the at least one or more sensors 14 in association with sensor chip 27, the LED interface 35, the GPS module 31, batteries 30 and 34, wireless module 29, and any other associated components. Other user interfaces, as discussed below, also can be used. The locations and layout of these various components, as shown in FIG. 3, can vary depending upon the size of and/or need for the components.

More specifically, in one embodiment, a sensor 14 is connected to micro-computer 28, which sits in the upper module 17. In this embodiment, sensor 14 exits the upper module 17 through a hole 17A at the top 17B of the module 17 and is directed downward to the water through attachment to the front 36 of the device 10. Other locations for sensor 14 also are possible, including, without limitation, an exit through the top 17B of module 17, but at other positions along the sides of module 17, an exit through a side of module 17, or location at an exit through lower module or base 16. These multiple locations can also allow a single module 17 to have multiple sensors 14. The sensor tip 14A typically includes the direct sensor components as needed for the water parameter being tested. Such components are known to those with skill in the art and include the mechanical system of the sensor 14 as well as associated software for use with the Arduino and conversion of data readings. Depending on the parameter being tested and the associated sensor 14, the sensor tip 14A may be submerged within the water, while, in other embodiments or interchangeable modules 17, tip 14A may not be fully exposed to the water. In this same respect, sensors 14, in an alternative embodiment, can be located in the lower module.

The removable modular component system of device 10 allows users to switch out the testing capability of the device. Depending on the needs of the user, the sensors 14 can be varied. Scientists and water quality inspectors can use modules 17 that contain high quality sensors 14, whereas citizens or residents in third-world countries can use the most basic of sensors 14 to test their water. The position, spacing, and amount of modules 16 and 17 can vary within the spirit and intended uses of the invention. While the upper module 17 sits on top of the lower module or base 16 in a "stacked" design in one embodiment, other configurations can be used, including a side-by side configuration. Modules 16 and 17 have an interlocking feature that allows module 17 to attach in a secure but detachable manner to module or base 16. This interlocking feature can be provided by heavy duty Velcro™, as one example, and other detachable interlocking mechanisms can be used as well.

Floatation Assembly. A flotation assembly 13 is attached to the exterior of the lower module 16. In the embodiment shown in FIGS. 1 and 2, the flotation assembly 13 can be comprised of two types of foam: (1) circular, hollow tubes of polyethylene 13A, and (2) water resistant Styrofoam™ 13B. The circular tubes 13A line each edge of the lower module 16 except for the side in which the sensor 14 is located. As shown in FIG. 1, tubes 13A are positioned around sensor 14 and sensor tip 14A The water resistant Styrofoam™ 13B is placed on the bottom of the lower module or base 16, and acts to keep the lower module or base 16 out of the water.

The positioning of the flotation assembly 13, which serves to keep device 10 on the surface of the water, facilitates the operation of the device 10 in collecting data on surface water quality. This feature distinguishes device 10 from other testing devices and methods because the buoyancy and relatively small size of device 10 makes it adaptable for use testing pool water, well water, tap water, etc. More directly, device 10 can be adapted for use in any home or field water setting that has a need for testing. At the same, the design of the components of the floatation assembly can vary, as can the type of buoyant and water resistant materials used in the components. For example, instead of circular tubes and an additional flotation on the bottom of the device 10, the whole device 10 can sit in a boat-shaped floatation device, which only exposes the propellers and sensor to the water. Alternatively, the flotation assembly 13 can be added onto the side or bottom of the device 10—depending on the placing of the other modules. If a lighter material for the modules 16 and 17 is used, or the overall weight of the device 10 is reduced, some components of the flotation assembly 13 may be removed.

Propellers and Motor System. In the embodiment shown in FIGS. 1, 2 and 4, the propeller assembly 12 are a part of the motor system 19 (located in the lower module or base 16), and are the only part of the motor system or base 16 that are in contact with the water. In one embodiment, the design of each propeller 15 can best be described as a "wheel," with a circular center 15A and six blades or slats 15B extruding from the center 15A at an angle from the radius of the wheel. This design reduces water resistance. The propellers 15 are attached on either end of an axle 20 that runs through the lower module or base 16, thereby putting a propeller 15 on opposite sides of the device 10. In one embodiment, the rotational movement of the axle 20 is controlled by one or more motors 19A and 19B, with corresponding gears 18A and 18B. The motors 19A and 19B are connected to a battery pack 24 and a remote control chip 22 so that the user, on land, can control the motor system 19 with a remote control device 25.

The above propeller design can vary, and any standard propeller design can be used, including, without limitation, paddle wheels, or any other wheel containing the described features. In addition, the design of the motor system and propulsion system can be slightly modified, as a hull design, rudder system, or other designs associated with boats, ships, or other aquatic robots can be incorporated.

Steering System. In the embodiment shown in FIGS. 1, 2 and 4, the motor system 19 can move both the propellers 15 in a synchronous manner such that device 10 can only move forward and backwards. However, in other embodiments device 10 includes a steering system. For example, each side propeller 15 can be independently controlled, on independent axles, in forward and backward movements so that the device 10 can turn right or left. In addition, the device 10 alternatively can incorporate a rudder system attached to module or base 16, similar to that used by a boat. Lower module or base 16 also can include a hull to help stabilize device 10 in the water. The location of a rudder system and hull would need to be coordinated with the location of the flotation assembly 13 and sensor 14. Other steering options, such as active wheel steering which will allow the device 10 to turn 360 degrees, can be incorporated in order to provide directional flexibility to device 10.

Water Testing and Sampling. The device 10 tests water by traveling in a water way (or any source of water e.g. pools, wells, tap water, etc.), and using the at least one sensor 14 (which is attached preferably to the front 36 of the device 10) to test the water in real time. Users can read all the collected data on their portable laptop or smartphone device. As such, users can identify the amount of chemicals in their water, and determine if the quantity is too high, too low, or normal. The device 10 of the present invention can also send the time, date, and location of where water quality data is collected via the GPS module 17 and wireless module 29, as discussed above. As a result, the device 10 allows for a very easy testing and analyzing process, and limits the need to do several extra steps to receive data. More directly, the device 10 is novel and beneficial in its ability to test water in real time, and avoid the time-consuming and inconvenient process of collecting samples and analyzing them on shore or in a lab.

At the same time, the device 10 is not limited to only testing real life samples. A component can be added to the device 10, such as assembly trailing from the back of the device or a mechanical "arm," crane, or similar mechanism that can reach out, scoop up a sample of water, and bring it back to the user on land. In addition to collecting physical water samples in this manner, the device 10 can also include components capable of collecting sediment samples from the shores of the water way, or underneath the surface water. These latter components can include the same arm or crane mechanism described above (with the collected sample being stored until it is intercepted by a user on land.

Figure 6:
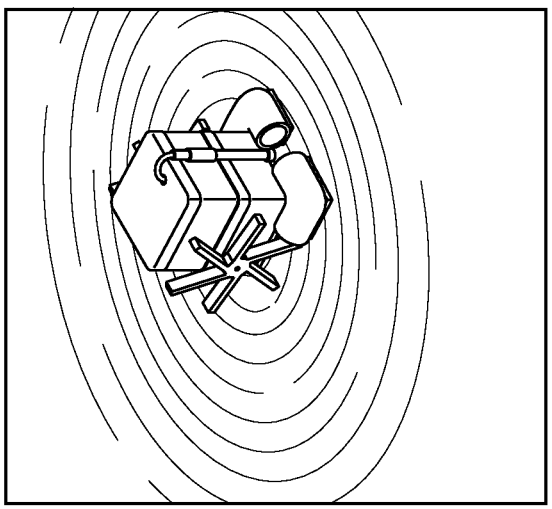
FIG. 6 is one embodiment of a serial monitor interface for the device shown in FIG. 1.
Figure 7:
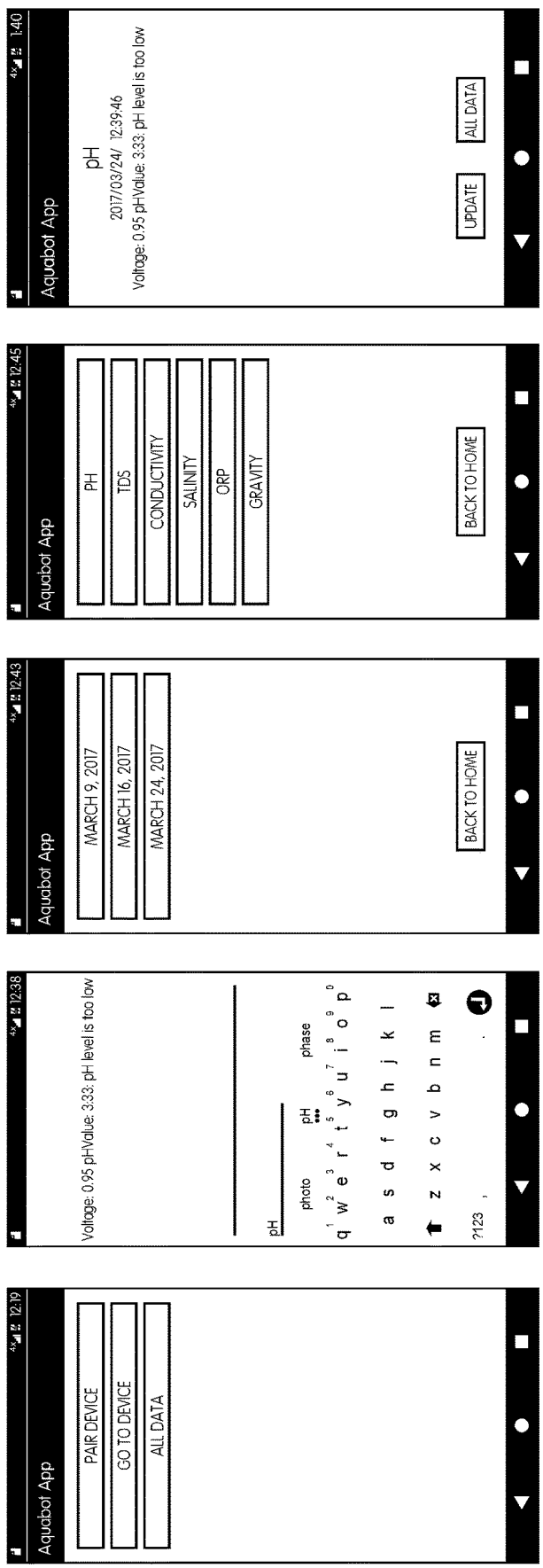
FIG. 7 is one embodiment of a smartphone application interface for the device shown in FIG. 1.
Figure 8:
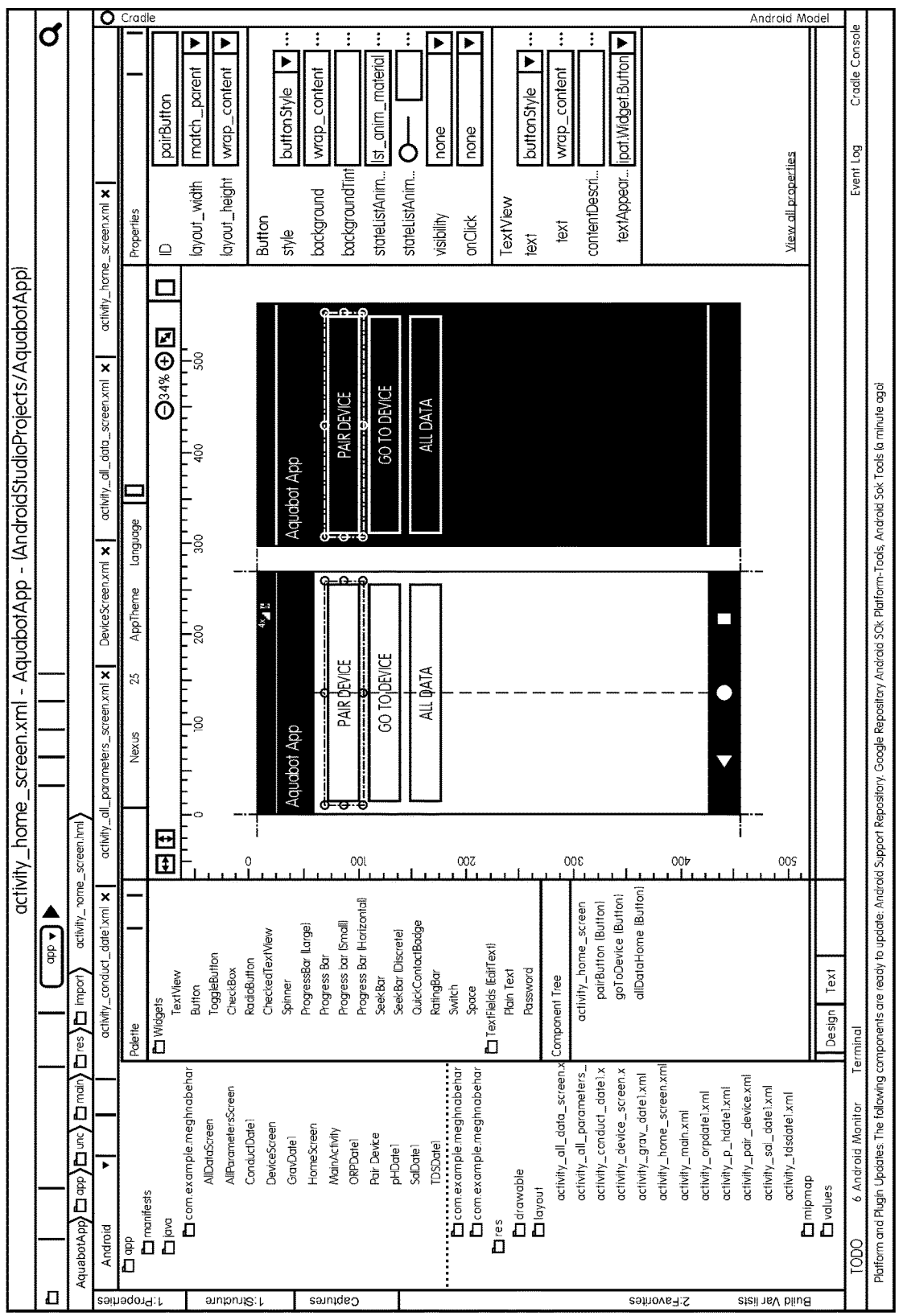
FIG. 8 is one embodiment of a programming application layout used with the device shown in FIG. 1.
Figure 9A:
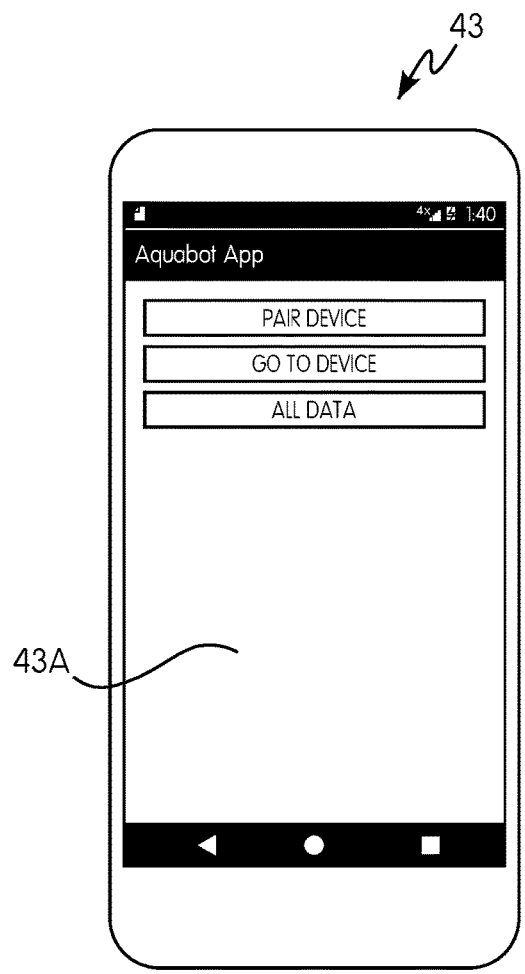
FIG. 9A is one embodiment of the front screen of a smartphone application interface used with the device shown in FIG. 1.
Figure 9B:
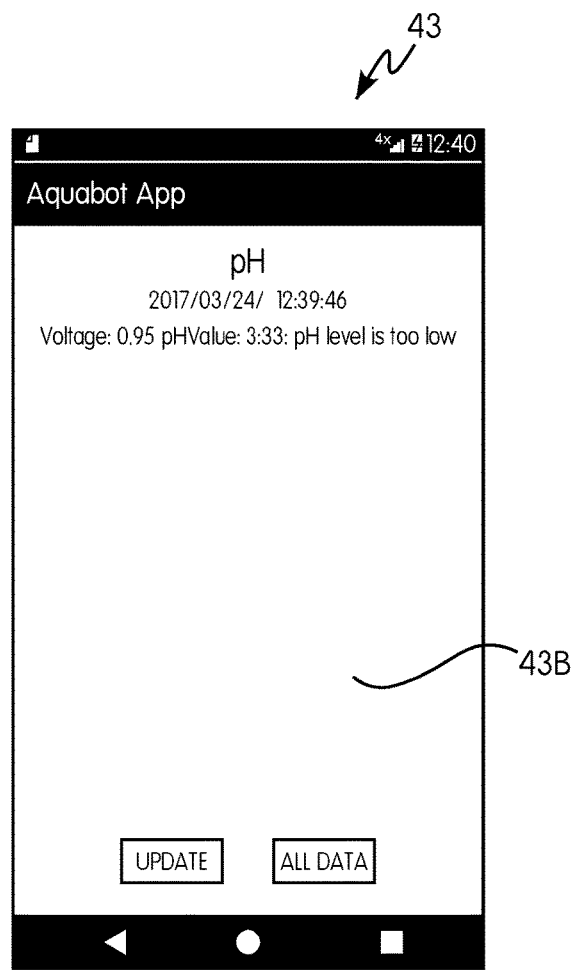
FIG. 9B is one embodiment of an internal screen showing pH results in the smartphone application interface shown in FIG. 9A.

GPS Module and Interfaces. The GPS module 17 and LED interface 35 of the device 10 provide data, collected by the device 10, for the user. The GPS module 17 can indicate the time, date, location, and altitude of where each piece of data is collected, and provide this information in association with the water sampling data. All of this data can appear either on a portable laptop or smartphone device of a user (who can be running a scientific test or collecting data as a homeowner, for example). FIG. 6 provides an example of a serial monitor interface 40 that a user would see of the pH testing. FIG. 7 provides a further example of a smartphone application interface 41. FIG. 8 shows an example of a programming application layout 42, and FIGS. 9A and 9B show an example of an application interface 43 on a smart phone, with home screen 43A shown at FIG. A and a screen 43B showing pH test results.

Figure 10A:
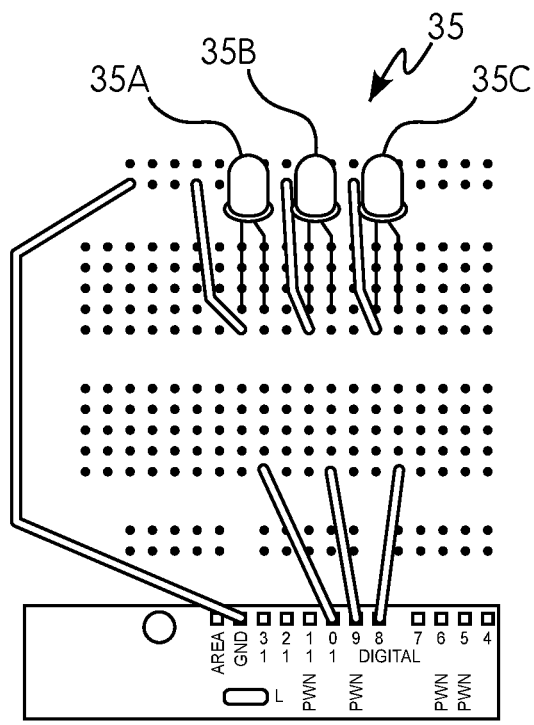
FIG. 10A is one embodiment of an LED interface for the device shown in FIG. 1.
Figure 10B:
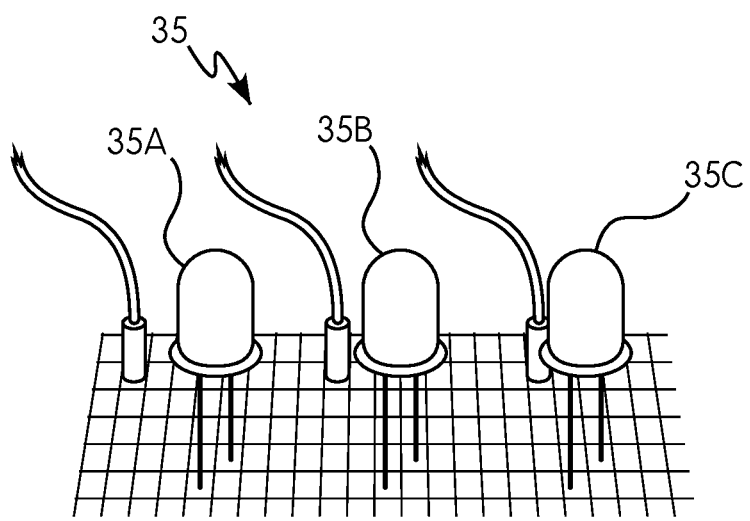
FIG. 10B is a close-up of the LED lights of the LED interface in FIG. 10A.

As described above, the LED interface 35 is located in the upper module 17 of the device 10 and, in one embodiment can emit color patterns to signal water quality information. For example, and as shown in FIGS. 10A and 10B, the LED interface can either blinks a red light 35A, green light 35B, or yellow light 35C associating with the quality of water (with red meaning a parameter is too high; green meaning it is normal; and yellow meaning it is too low). This is an important aspect of device 10, as this interface 35 allows the device 10 to be used by a larger demographic group of users.

The device 10 can also include one or more other interfaces 45, such as an LCD interface, an audio interface, and a paper testing interface. The LCD interface can collect the average amount of the parameter being tested, and display it on an LCD screen located on the device 10. The audio interface can emit a beep or any warning signal when water quality is not healthy. The paper testing interface can give the quality of water on a paper test strip attached to the device 10, which can then be intercepted by a user on land once it has been exposed to the water. The device 10 can be adapted to include additional interfaces within the spirit and function of the device 10 and thereby further allow the device 10 to be used across multiple applications and a wide range of users. The LCD interface and audio interfaces connect to the micro-computer 28 and battery pack 30. The paper testing interface can be its own separate component, and preferably includes an external component mounted on an exterior side of the device 10 so that this interface comes into contact with the water.

Figure 11:
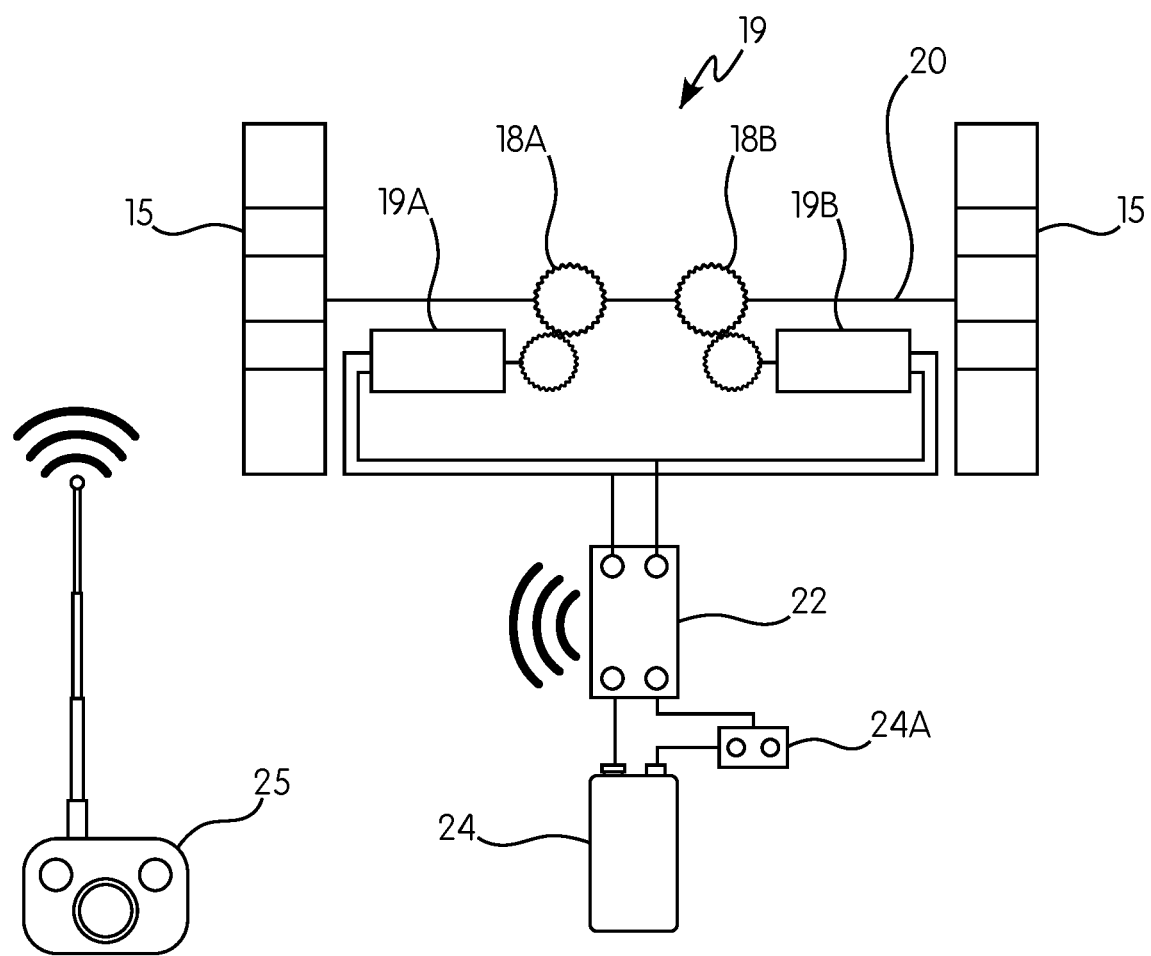
FIG. 11 is one embodiment of a block diagram of the motor system of the device shown in FIG. 1.

Wireless Connection. Two important components of the device 10, in one embodiment, are its remote control 25 and wireless module 29. As shown in FIG. 11, the remote control 25 interacts with motor system 19 to control motors 19A and 19B. As further shown in FIG. 11, battery 24 can have an on/off switch 24A.

The wireless module 29 allows data to be sent from device 10 to a user's cellphone or laptop. The remote controller 25 allows the motor system 19 to run wirelessly. While the wireless feature of the device 10 is a preferred component, the technology used to achieve wireless usage can be varied interchangeable. For example, alternatives can include, without limitation, Bluetooth®, Infrared Wireless, Ultra Wideband, Induction Wireless, and other similar technologies.

It will be understood that each of the devices, elements and components described above, or two or more together, may also find a useful application in other types of constructions differing from the types described above. While the invention has been illustrated and described in certain embodiments, it is not limited to the details shown, since it will be understood that various omissions, modifications, substitutions and changes in the forms and details of the device illustrated and its operation can be made by those skilled in the art without departing in any way from the spirit of the present invention.

What is claimed is:

1. An aquatic robotic assembly for testing and monitoring water quality parameters comprising:
   a waterproof base comprising a remote-controlled motor assembly, a propulsion assembly, a power source, and a flotation assembly; and
   at least one waterproof upper module that detachably connects to the base and includes a sensor assembly, the sensor assembly comprising at least one sensor for use in testing and monitoring a water quality parameter, a micro-computer interconnected with the at least one sensor for reading sensor data input from the at least one sensor and converting the sensor data input to a format readable by a user, a wireless transmitter for transmitting the converted data to the user, and a power source.

2. The robotic assembly of claim 1, wherein the upper module further comprises a GPS module for transmitting the location of the robotic assembly to the user during water testing.

3. The robotic assembly of claim 2, wherein GPS module provides and transmits, in association with the converted sensor data input, the time, date, location, and altitude of where the sensor data input is collected.

4. The robotic assembly of claim 1, wherein the upper module further comprises an LED interface for providing a visual signal as to a water quality parameter.

5. The robotic assembly of claim 1, wherein the base further comprises a steering assembly.

6. The robotic assembly of claim 1, wherein the at least one sensor is attached to an external side of the upper module.

7. The robotic assembly of claim 1, wherein the at least one sensor has a sensor tip positioned to test and monitor a surface water quality parameter.

8. The robotic assembly of claim 1, wherein the at at least one sensor tests for water quality parameters selected from the group consisting of pH, oxidation reduction potential, total dissolved solids, conductivity, salinity, ammonia, nitrite, nitrate, and specific gravity.

9. The robotic assembly of claim 1, wherein the upper module contains one or more interfaces selected from the group consisting of an LED interface, an LCD interface, an audio interface, and a paper testing interface.

10. The robotic assembly of claim 1, wherein the wireless transmitter also receives wireless transmissions from the user.

11. The robotic assembly of claim 1, wherein two or more additional upper modules provide alternative sensor assemblies for testing variable water quality parameters and interchangeable connection to the base and use with the robotic assembly.

12. The robotic assembly of claim 1, wherein the propulsion assembly comprises one or more propellers.

* * * * *